United States Patent [19]
Layer et al.

[11] Patent Number: 5,529,463
[45] Date of Patent: Jun. 25, 1996

[54] PUMPING APPARATUS FOR PERFUSION AND OTHER FLUID CATHETERIZATION PROCEDURES

[75] Inventors: James Layer, Cooper City, Fla.; Andrea Slater, Somerville, N.J.; Karl Weissinger, Miami, Fla.

[73] Assignee: Cordis Corporation, Miami Lakes, Fla.

[21] Appl. No.: 229,913

[22] Filed: Apr. 19, 1994

[51] Int. Cl.⁶ .............................. F04B 17/00; A61M 5/20
[52] U.S. Cl. .......................... 417/403; 417/460; 417/521; 604/152; 128/DIG. 12
[58] Field of Search .................................... 417/403, 460, 417/521; 604/152; 128/DIG. 12

[56] References Cited

U.S. PATENT DOCUMENTS

| | | |
|---|---|---|
| 2,393,175 | 1/1946 | Laskey . |
| 2,545,315 | 3/1951 | Sproull . |
| 2,896,621 | 7/1959 | Rodrigues . |
| 3,099,260 | 7/1963 | Birtwell . |
| 3,259,077 | 7/1966 | Wiley et al. . |
| 3,447,479 | 6/1969 | Rosenberg . |
| 3,818,907 | 6/1974 | Walton . |
| 4,255,096 | 3/1981 | Coker, Jr. et al. ...................... 604/152 |
| 4,490,331 | 12/1984 | Steg, Jr. . |
| 4,634,430 | 1/1987 | Polaschegg . |
| 4,708,603 | 11/1987 | Kubo ....................... 417/521 |
| 4,867,742 | 9/1989 | Calderon . |
| 4,919,597 | 4/1990 | Kistner ..................... 417/403 |
| 4,985,014 | 1/1991 | Orejola . |
| 5,066,282 | 11/1991 | Wijay et al. . |
| 5,195,879 | 3/1993 | Reese et al. ............................ 417/521 |
| 5,325,867 | 7/1994 | Skrabel et al. ......................... 604/152 |

FOREIGN PATENT DOCUMENTS

| | | | |
|---|---|---|---|
| 2175352 | 5/1985 | United Kingdom ................... | 417/403 |

OTHER PUBLICATIONS

Serial No. 186,667—Layer, "Pumping Apparatus for Perfusion and Other fluid Catherization Procedures" filed Jan. 25, 1994.

Serial No. 223,869—Reed et al.—"Pumping Apparatus for Perfusion and Other Fluid Catherization Procedures" filed Apr. 19, 1994.

*Primary Examiner*—Richard A. Bertsch
*Assistant Examiner*—William Wicker
*Attorney, Agent, or Firm*—Lockwood, Alex, Fitzgibbon & Cummings

[57] ABSTRACT

A pumping apparatus which is particularly useful in catheterization procedures has two pumps supported in a parallel arrangement. The pumps are engaged by an actuating rod connected to a power cylinder which reciprocates longitudinally between the two pumps. The two pumps are held within the housing such that only the plunger element of one pump is capable of movement in response to the actuating member while only the barrel element of the other pump is capable of movement in response to the actuating member. By way of this linkage, during movement of the actuating rod, one pump performs a pumping stroke while the other pump performs a suction stroke.

23 Claims, 3 Drawing Sheets

PUMPING APPARATUS FOR PERFUSION AND OTHER FLUID CATHETERIZATION PROCEDURES

BACKGROUND AND SUMMARY OF THE INVENTION

The present invention relates generally to equipment employed in the performance of perfusion catheterization procedures, and more particularly, to a pumping apparatus which interconnects an aspiration catheter with a percutaneous transluminal coronary angioplasty (PTCA) catheter or the like to provide a constant, preselected flow of body fluids through the catheter.

The use of inflatable balloon catheters in the treatment of coronary conditions is widespread. Balloon catheters are commonly used to expand blockages in arteries. These blockages are a narrowing of an artery or other body vessel, and are referred to as a stenoses. In PTCA procedures, a guide catheter is introduced into the artery of the patient and guided through the artery until the distal tip of the catheter is at the desired location of the coronary artery near the stenosis. A dilation catheter having an inflatable balloon affixed to its distal end is introduced along the guide catheter and advanced into the patient until the balloon end is located at the stenosis. The balloon is subsequently inflated to expand it against the artery walls to expand, or dilate, the artery and compress the stenosis. This expansion can remove all of or a significant portion of the blockage when the balloon is inflated against the arterial walls for a preselected time or repeatedly inflated and deflated in a cycle to match that of the heartbeat of the patient.

Once the artery has been expanded, the balloon is deflated and it and the guide catheter is removed so the blood again may flow on its own through the artery. Restenosis is a condition where the arterial wall has been initially expanded by the balloon and the arterial blockage is open but the arterial wall contracts and adopts all of or part of its original, restricted state sometime after the balloon is deflated and removed. The rate of restenosis is believed to be lowered if longer inflation times are used during balloon catheterization procedures.

The use of longer balloon inflation times may promote the occurrence of ischemia of the cardiac muscles. Ischemia is a local deficiency of oxygen in an area of the body caused by an obstruction in the blood vessels supplying blood to that area. To prevent ischemia, perfusion catheters are used in association with coronary angioplasty catheters. Perfusion catheters are catheters which permit the continuous flow of blood through the blockage during the inflation of the balloon in the artery.

The perfusion of blood through a balloon at the distal end of a catheter may be accomplished by a balloon having one or multiple passages or lumens which define flow channels extending through the balloon from one end to the other. These passages permit flow of blood past the balloon and through the blockage. A reliable pump must be used to pump blood continuously past the balloon through the balloon passages. In order to avoid ischemia, a specific flow rate past the balloon, such as 60cc per minute is desirable. Generally, perfusion catheters have lumens which are very small and have minute diameters on the order of approximately three mils (0.003 inch). Any external pump used in such perfusion procedures to pump blood through these size catheters must provide a continuous flowrate of blood at high pressures which may approach 300 psi. These high pumping pressures are needed in order to pump blood through small lumens of these catheters, rather than rely upon the patient's heart to pump blood through the lumens past the balloon inflation area. The external pump draws blood from the patient by way of an aspiration catheter and circulates it back through the perfusion catheter and past the distal end of the balloon.

External blood pumps are well-known and have been commonly used for regulating blood through coronary arteries during open-heart surgeries. These pumps generally provide a low pressure output and are not capable of supplying the necessary high pressure to pump blood at the predesired flowrate through the small lumens used in perfusion catheters. A positive displacement pump which uses a conventionally powered piston may create a pressure pulse during its pumping stroke which may result in a pressure transient occurring during pumping. If a single-stroke piston pump is used, it may only at best provide intermittent blood flow because after every pumping stroke, a reversal or suction stroke, must be performed to refill the pump piston. A need therefore exists for reliable perfusion pump which can pump continuously and develop the large pumping pressures needed for perfusion through small diameter catheters.

External perfusion pumps are well known, such as the one described in U.S. Pat. No. 5,066,282 issued Nov. 19, 1991. This patent is directed to a perfusion pump with a pulsation-damping mechanism that serves to smooth out pressure pulses of the pump during pumping. This pump contains only one pumping chamber and relies upon a reservoir to be continuously filled with blood or similar body fluid. No provision is made in this patent for the components of the pump to be entirely disposable, and, due to the pressure damping means incorporated in the pump, it may be expensive to manufacture and difficult to clean.

Other external pumps are known which use syringes as their primary components, such as that described in U.S. Pat. No. 3,447,479, issued Jun. 2, 1967. This patent describes various arrangements of syringe pumps which perform alternating suction and pumping strokes. In the multiple syringe pump arrangement shown in this patent, four syringe pumps are powered by a motor-driven eccentric cam. However, return springs must be used on the plungers of these pumps in order to ensure the prompt return of the pump plungers to their original positions within the syringes. This mechanism is complicated and a possibility exists that the springs and cam may not always reliably power the pumps through a complete suction and pumping cycle because of wear.

The present invention is therefore directed to an external pumping apparatus for use in catheterization procedures, and particularly in perfusion catheterization which continuously and reliably both withdraws blood from a patient and reintroduces the blood back into the patient.

In accordance with one aspect of the present invention, a housing member is provided which supportingly engages two positive displacement pumps, each of the pumps having a plunger slidable within a pump chamber, the plunger of one pump and the chamber of the other pump being fixedly mounted to the housing so as to prevent movement relative to the housing. The one pump chamber and the other pump plunger engage an actuating member slidable within the housing. When the actuating member moves in response to movement of a power cylinder, it imparts a pumping action in the one pump and a suction action in the other pump. Movement of the actuating member in the opposite direction induces a reverse movement in the pump components, so that the one pump will perform a suction stroke while the other pump performs a pumping stroke, whereby the pumping apparatus provides a continuous flow of blood during its operation.

In another aspect of the present invention, two syringe pumps are disposed within a housing, each of the syringes having a plunger slidable within a barrel portion and the housing having two channels in which the syringes are situated. One housing channel engages the plunger of one pump and restrains it from movement relative to its barrel portion, while the other housing channel engages the barrel portion of the other pump and restrains it from movement relative to its plunger. The actuating member reciprocates in the housing parallel to the longitudinal axes of the syringe pumps. The actuating member engages a double acting piston powered by a hydraulic fluid or gas. At any given time during operation of the apparatus, the actuating member engages a plunger member of one pump and a barrel portion of the other pump so that in response to any movement of the piston, the actuating member drives one of the two pumps in a pumping mode and the other pump in a suction mode.

Accordingly, it is an object of the present invention to provide an external perfusion pumping apparatus for use in PTCA and other related catheterization procedures which can readily supply a continuous supply of blood or other body fluids at high pumping pressures required for the perfusion of these fluids through catheter minute diameters.

Another object of the present invention is to provide a pumping apparatus having multiple pump elements supported in a housing, the pumping apparatus including a fluid powered cylinder operatively engaging the pump elements to simultaneously drive one pumping element in a pumping stroke and another pump element in an aspirating, or suction stroke, whereby the pumping apparatus provides a continuous supply of body fluids to a perfusion catheter or other catheter.

Still another object of the present invention is to provide a pumping apparatus for use in perfusion catheterization wherein the pumping apparatus includes two syringe pumps, each having a plunger component slidable within a barrel component, the plunger and barrel components cooperating to define a pumping chamber of variable volume in each syringe pump, each of the syringe pumps being supported within a housing, the two pumps being interconnected by a rod operatively associated with a fluid cylinder wherein movement Of the fluid cylinder imparts a like movement to the actuating member, the fluid cylinder operating in a reciprocating manner such that at any instant during operation of the pumping apparatus, one of the two syringe pumps is constantly withdrawing, or aspirating, blood from a blood source, while the other syringe pump is constantly pumping blood from the blood source into the patient to achieve a continuous flow of blood through the apparatus and into the patient at a preselected flowrate to prevent ischemia or other injury to the heart of the patient from prolonged lack of blood.

Still yet another object of the present invention is to provide an improved pumping apparatus for use in perfusion and other catheterization procedures wherein two syringe pumps are powered by a fluid cylinder such that one syringe pump is maintained in a pumping mode while the other syringe pump is maintained in a suction mode and wherein the fluid cylinder ensures that each of the two syringe pumps returns to its initial operating position after movement by the fluid cylinder without the necessity for return springs or the like.

These and other objects features an advantages of the present invention will be clearly understood through consideration of the following detailed description.

BRIEF DESCRIPTION OF THE DRAWINGS

In the course of the following detailed description reference will be frequently made to the accompanying drawings in which.

DETAILED DESCRIPTION OF THE PREFERRED EMBODIMENTS

Figure 1:
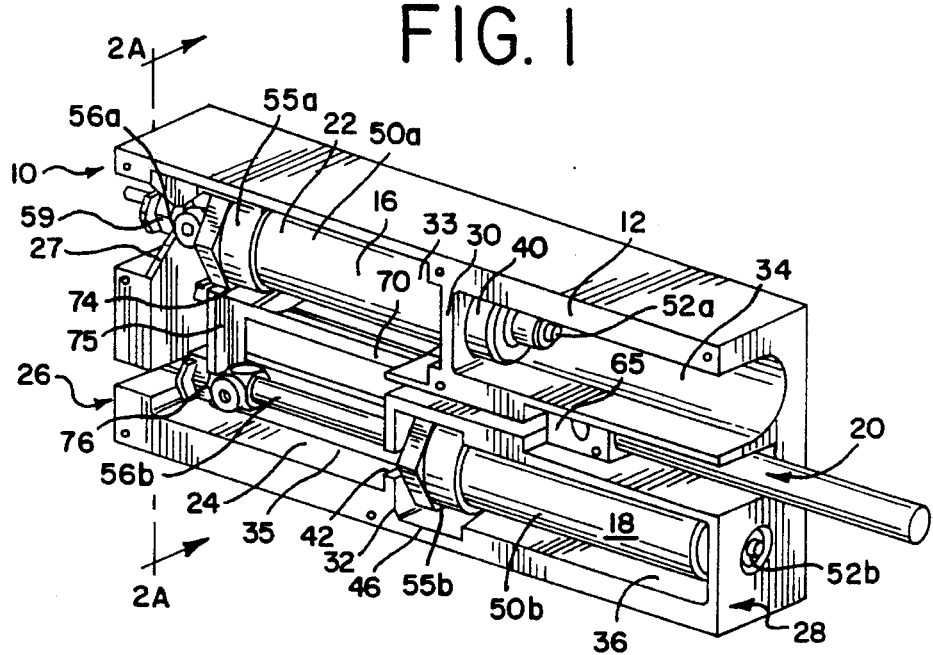
FIG. 1 is a perspective view of a pumping apparatus constructed in accordance with the principles of the present invention.

Referring to the drawings, FIG. 1 illustrates an external pumping apparatus, generally designated as 10, for continuously pumping blood or any other body fluid, into and out of a patient's body during a catheterization procedure, such as PTCA. The apparatus 10 includes a housing portion 12, an actuating assembly 14, and a pair of positive displacement pumps, illustrated as syringe pumps 16, 18. The pumps 16, 18 need not be limited to the syringe pumps shown, but may take the form of any other suitable pumping means so long as one of the pump components may be moved relative to the other pump component. The housing portion 12 further includes a means for driving the actuating member 14, generally illustrated as a power cylinder 20.

Figure 5:
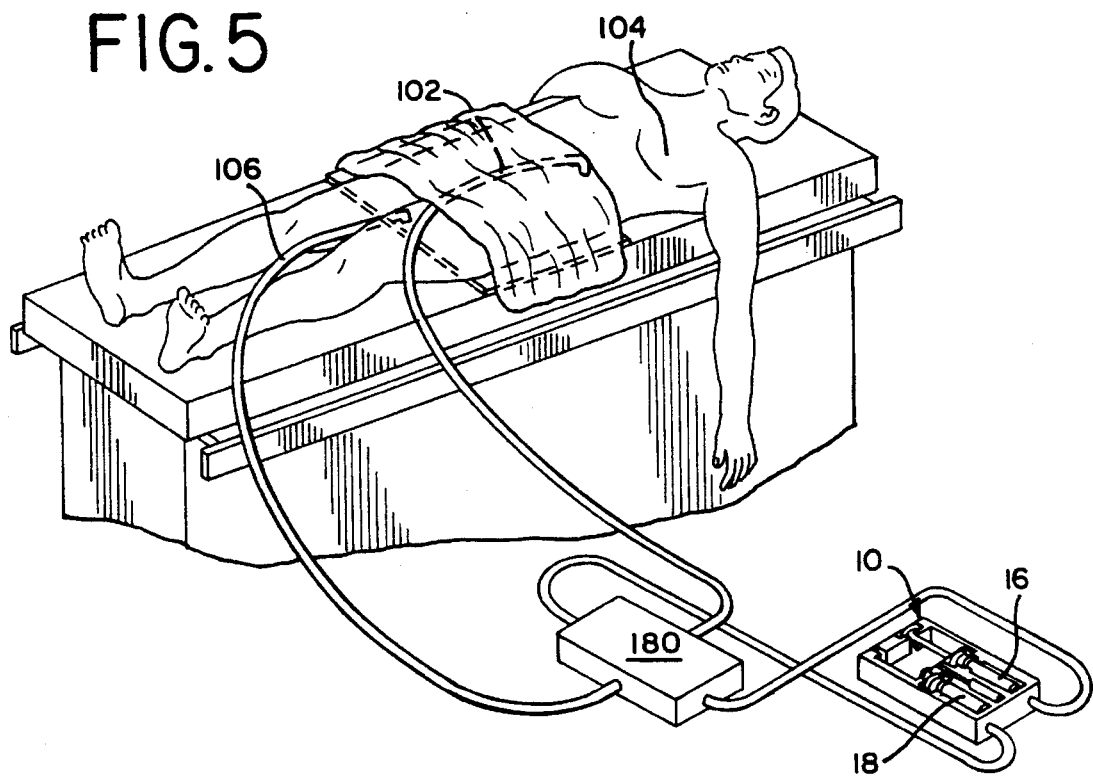

The pumping apparatus 10 of the present invention is particularly useful during catheterization procedures which require perfusion, such as PTCA, wherein a PTCA catheter 102 is inserted into an artery of a patient's body 104 (FIG. 5) and guided to an area of an artery where a blockage, or stenosis has occurred. The PTCA catheter includes an inflatable balloon (not shown) which is inflated when the balloon is located in proximity to the blockage site. During inflation, the balloon is inflated and expanded against the arterial walls and the stenosis in order to exert pressure on the artery and stenosis in order to widen the opening through the blockage. One or more lumens (also not shown) extend through the PTCA catheter and through the balloon. These lumens provide passages for the blood to be perfused into the patient past the blockage to prevent the deficiency of blood and the oxygen it carries to the areas distal of the balloon.

The patient's own blood or body fluids are used in a PTCA or other catheterization procedure by means of an aspiration catheter 106 (FIG. 5) inserted into a conveniently located artery of the patient. Blood may be drawn through the aspiration catheter 106 by one or more pumps 16, 18 of the pumping apparatus 10. The pumps are powered by a fluid cylinder 20 and are operatively coupled together such that as one syringe pump 16 is operating in a suction stroke to draw blood from the patient's body 104 through the aspiration catheter 106, the other syringe pump 18 is operating in a pumping stroke to pump blood previously drawn from the patient's body 104 and back into the patient via PTCA catheter 102.

Figure 4:
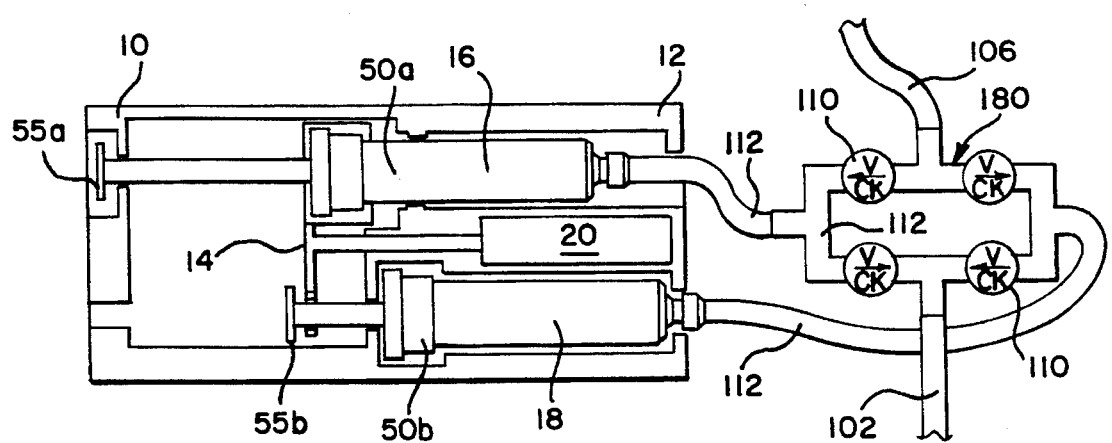
FIG. 4 is a schematic view of the pumping apparatus of FIG. 1 used in conjunction with a fluid flow regulating assembly; and, FIG. 5 is an overall view of a PTCA system using the pumping apparatus of FIG. 1.

A suitable flow regulating means, such as check valves 110 (FIG. 4) and associated tubing 112, is preferably used in association with the present invention, and is illustrated as arranged in-line with the aspiration and PTCA catheters to synchronize and regulate the flow of body fluids into and out of the pumping apparatus 10.

Figure 2A:
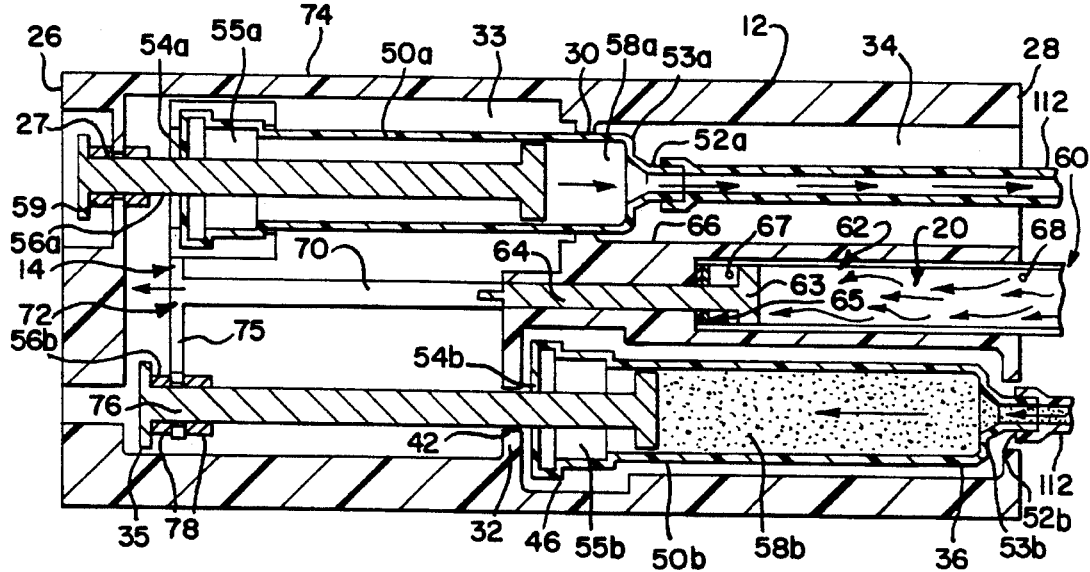
FIG. 2A is a cross-sectional view of the pumping apparatus of FIG. 1, taken along line A—A thereof, generally illustrating a first operating condition of the pumping apparatus.
Figure 2B:
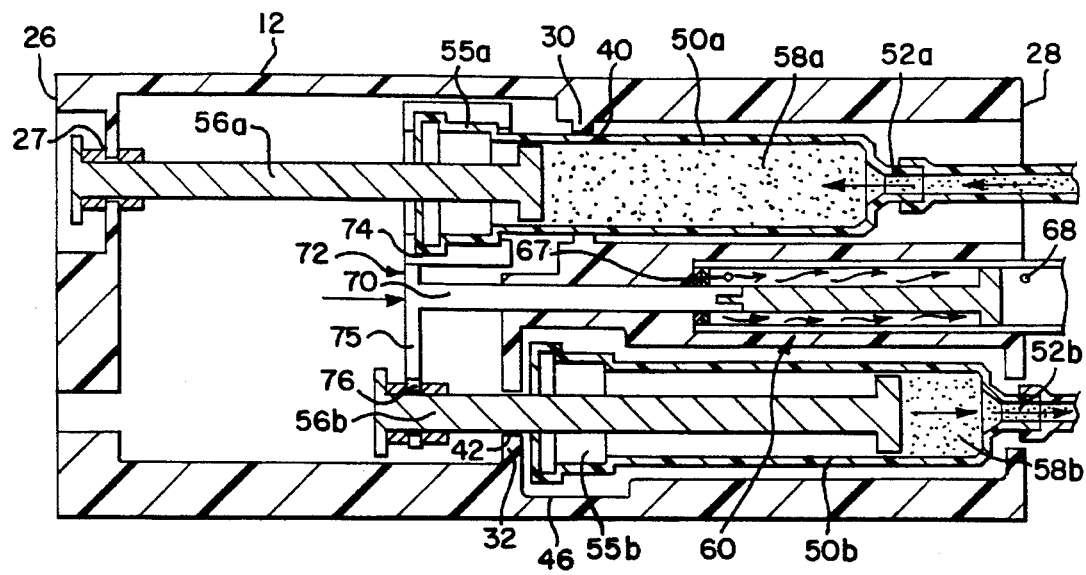
FIG. 2B is the same view as FIG. 2B, but generally illustrating a second operating condition of the pumping apparatus.

Returning now to the pumping apparatus 10, and focusing particularly on the structure of the housing portion 12 of the pumping apparatus 10, as illustrated in FIG. 1, the housing portion 12 is configured to synchronize the operating sequence of the two pumps 16, 18 such that while one pump is drawing blood from the patient, the other pump is pumping blood into the patient. This synchronization permits the pumping apparatus 10 to provide a continuous supply of blood or body fluids through the perfusion catheter 106. The housing portion 12 therefore includes two channels, or slots, 22, 24 disposed therein between housing opposing end portions 26, 28. The channels 22, 24 receive the first and second pumps 16, 18 as illustrated. As best depicted in the embodiment of FIGS. 1, 2A, 2B the channels 22, 24 may each include, at an intermediate location, a dividing wall 30, 32 which defines two compartments, or subchannels 33, 34, 35, 36 in each channel. Each dividing wall 30, 32 has an opening 40, 42 which, as explained below, permits movement of at least one of either the plunger or barrel component of each pump 16, 18 through its respective dividing wall.

The syringe pumps are conventional in nature, and include elongated cylindrical barrel portions 50a, 50b having outlet openings 52a, 52b disposed in one end 53a, 53b. The opposite ends 54a, 54b of the barrel portions 50a, 50b terminate in flanged end portions 55a, 55b which define the beginning of a pump chamber 58a, 58b within each barrel portion. A plunger portion 56a, 56b is received within each respective pump barrel portion 50a, 50b and reciprocates therein to perform alternating pumping and suction strokes in each of the pumps. The pumping chambers 58a, 58b of each pump have a variable volume which depends on the position of the pump plunger portions 56a, 56b with respect to the pump outlets 52a, 52b. This volume is the greatest where the plunger portions 56a, 56b are nearest the rear ends 55a, 55b of the barrel and is the least where they are nearest the pump outlet openings 52a, 52b.

In an important aspect of the present invention, the housing 12 includes a pair of channels 22, 24 which respectively house the pumps 16, 18 during operation of the apparatus. The plunger and barrel portions 56a, 50b of the first pump 16 are generally located within the first compartment 33 of the channel 22 so that the pump barrel portion 50a extends into the first channel dividing wall opening 40. There is a sufficient clearance between the opening 40 and the barrel portion 50a which permits movement of the barrel 50a longitudinally within the first channel 22 between its first compartment 33 and adjoining second compartment 34. The first channel endwall 26 incorporates a pump restraining means, such as slot 27, which receives the plunger portion 56a of first pump 16 and restrains the plunger portion 56a from movement relative to both the first pump barrel portion 50a and housing 12. The plunger portion 56a may include one or more stop members, such as nuts 59 on its shaft to serve as an adjustable stop by which the stroke of the plunger portion 56a in the barrel portion 50a may be set.

The second channel 24 of the housing 12 also has a structure which permits movement of only the plunger portion 56b within the channel 24 between the first and second compartments 35, 36 thereof. As illustrated, the second channel second compartment 36 houses the second pump barrel portion 50b and restrains it from any significant movement. A recess 46 may be formed in the second compartment 36 to receive the flanged end portion 55b of the syringe pump 18. The second compartment dividing wall 32 contains an opening, shown as a slot 42, which receives the plunger portion 56b of the second pump 18. Slot 42 permits slidable moment of the plunger portion 56b between the two compartments 35, 36 of the second channel 24.

In another important aspect of the present invention, the pumping apparatus includes a means for driving the two pumps 16, 18, illustrated as an assembly 60 which includes a single-ended, double-acting fluid cylinder 20. The cylinder 20 is conventional in nature and has a double acting piston 62 slidable therein. The piston 62 includes a piston head 63 attached to a piston rod 64 extending longitudinally within the cylinder 20. The rod 64 extends outwardly from the cylinder 20 through a seal assembly 65 having one or more seal members 66 which provide a substantially fluid-tight seal between the rod 64 and the cylinder end. The seal assembly 65 permits displacement of the rod 64 in and out of the cylinder 20 in response to fluid introduced ahead or behind of the piston head 63 through suitable ports 67, 68 to drive the piston 62 in either direction. The introduction of this fluid into the cylinder 20 is controlled by a suitable fluid control means (not shown) well known in the art.

The piston rod 64 may engage an actuating member 14 which extends within the apparatus housing 12 between the two channels 22, 24. The actuating member 14 may include a shaft member 70 having a yoke portion 72 which engages the barrel portion 50a of one pump 16 and the plunger portion 56b of the other pump 18. The yoke portion 72 has a carriage element 74 which engages the barrel flanged end portion 55a of first pump 16. The carriage element 74 may be generally U-shaped as illustrated and preferably engages more than half of the circumference of the barrel portion 50a in order to assure it securely grip the barrel portion 50a and apply a balanced driving force to the pump 16 to drive the barrel portion 50a through the dividing wall opening 40 evenly and without interference with the dividing wall 30.

On the opposite side of the actuating member 14, an arm element 75 extends outwardly and engages the plunger portion 56b of the other pump 18. The arm element 75 may include a slot 76 as shown which fixedly engages the plunger portion shaft. Suitable stop members, such as nuts 78, connect the actuating member 14 to the second pump plunger portion 56b.

As can be seen from the Figures, the actuating member 14 simultaneously engages two different components of the two pumps 16, 18 and moves them in the same direction to effect alternating pumping and suction strokes in the two pumps. The actuating member 14 also returns the pumps 16, 18 to their initial position without the need for return springs or other similar mechanical means. The mechanical operation of the present invention is best understood by reference to FIGS. 2A and 2B, which illustrate movement of the pumping apparatus components 10 under two distinct operating conditions.

In FIG. 2A, the cylinder 20 is pressurized at one end as fluid flows into the cylinder through the cylinder port 68. As the fluid pressure in the cylinder rises, the cylinder piston head 63 displaces in the cylinder (toward the left in FIG. 2A), and the cylinder rod 64 extends out of the cylinder. In doing so, it imparts a linear movement to the actuating member 14 which moves the barrel portion 50*a* of the first pump 16 rearwardly toward its plunger portion 56*a* to drive body fluid contained in the first pump pumping chamber 58*a* out of first pump 16 through the outlet opening 52*a*. Simultaneously, actuating member 14 drives the second pump 18 in a suction stroke, whereby its plunger portion 56*b* is moved rearwardly in the barrel portion 50*b* to draw body fluid into the second pump pumping chamber 58*b* through its outlet opening 52*b*.

FIG. 2B illustrates the operation of the apparatus 10 in a second operating condition wherein fluid is introduced into the cylinder on the opposite side of the piston head 63 through the cylinder port 67 to drive the piston in a direction opposite that shown in FIG. 2A. In this movement, the piston head 63 is driven to the right as shown in FIG. 2B, and the actuating member 14 is likewise drawn to the right. The actuating member 14 through its yoke 72 and arm 75, moves the first pump barrel portion 50*a* away from the plunger portion 55*a* thereof to draw body fluid into the first pump pumping chamber 58*a* through opening 52*a*. Simultaneously, the actuating member 14 drives the second pump plunger portion 55*b* forwardly in the barrel portion 50*b* to drive body fluid out of the pumping chamber 58*b* through second pump opening 52*b*. The body fluids are conveyed to the various catheters by way of tubing 112.

The fluid used in the cylinder 20 may by a traditional hydraulic fluid or it may be a gaseous fluid, such as compressed air or carbon dioxide.

Figure 3:
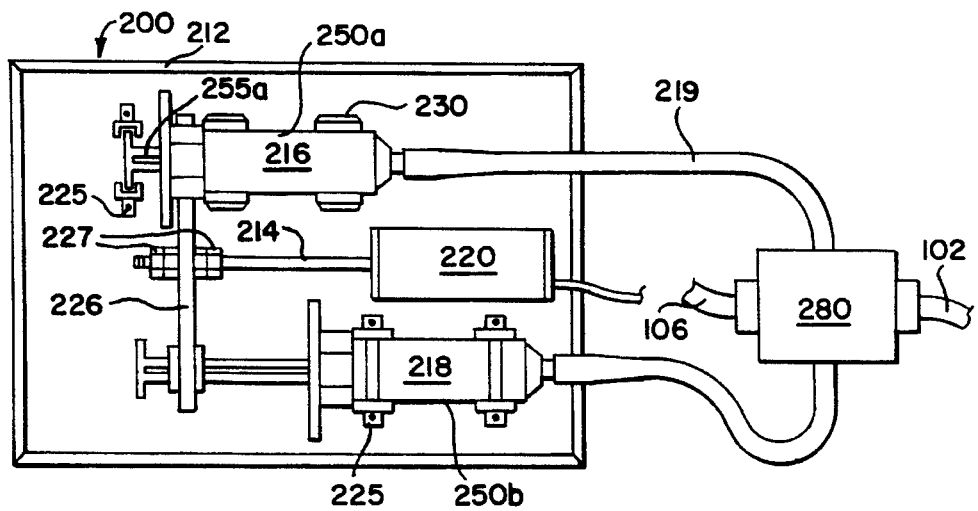
FIG. 3 is a plan view of another embodiment of a pumping apparatus constructed in accordance with the principles of the present invention.

FIG. 3 illustrates a second embodiment of a pumping apparatus 200 constructed in accordance with the principles of the present invention wherein the apparatus includes a base 212 which supports two syringe pumps 216, 218 generally parallel to each other. A fluid cylinder 220 is disposed between the two pumps and has an actuating rod 214 extending through one end. The plunger portion 255*a* of the first pump 216 is fixed to the base 212, as is the barrel portion 250*b* of the second pump 218. These components may be fixed to the base 212 by way of clips 225 or any other suitable means. The barrel portion 250*a* of the first pump 216 is preferably supported on the base 212 by saddle members 230 which allow the barrel portion 250*a* to slide back and forth in response to movement of the actuating rod 214.

A driving link 226 is connected to the actuating rod 214 and may be positioned on the rod with nuts 227. The link 226 engages the first pump barrel portion and the second pump plunger portion 255*b* so that they move linearly in response to movement of the actuating rod 214 in a manner similar to that described above. In this embodiment, as well as the embodiment shown in FIGS. 1–2A, the longitudinal axis of the rod 214 is preferably maintained on the base at the same horizontal plane as the longitudinal axes of the two pumps 216 and 218. The two pumps 216 and 218 connect with lengths of tubing 219 which lead to a fluid flow regulating device 280 which channels flow into and out of the pumping apparatus 200 into and out of the aspiration catheter 106 and perfusion catheter 102.

As mentioned above and as generally illustrated in FIG. 4, the pumping apparatus of the present invention is most effective when used in conjunction with a fluid flow regulating device which includes a plurality of check valves 110 arranged in-line with interconnecting tubing 112. The valves are disposed in the tubing and spaced apart so as to route flow from the aspiration catheter 106 to whichever of the two pumps performs a suction stroke and to route flow from the pump performing a pumping stroke to the perfusion catheter 102.

The pumping apparatus of the present invention is simple and convenient to use. The apparatus can be fabricated inexpensively and the pump elements thereof may be made of inexpensive disposable materials, such as polymers, thereby eliminating any necessity to clean and/or disinfect the apparatus after every use. The present invention therefore provides a pumping apparatus at minimal expense, which can perform the functions of multiple pumps. It has been determined through testing that present invention easily attains the high pumping pressures (approximately 300 psi) required to maintain a flow rate of 60 cc per minute to a patient's body through small diameter catheter.

While the preferred embodiment of the invention have been shown and described, it will be apparent to those skilled in the art that changes and modifications may be made therein without departing from the spirit of the invention, the scope of which is defined by the appended claims.

We claim:

1. A pumping apparatus for delivering a continuous flow of body fluid to a preselected location within a patient's body, comprising:

first and second pumps, each of the two pumps having a barrel portion defining a pump chamber and a plunger member slidably received within said barrel portion, each of said pump barrel portions having an outlet end for the passage of fluids from the pump chamber out of said pump, a support assembly supporting said first and second pumps together, said first and second pumps being supported such that each of said pump outlet ends is oriented in the same direction, the pumping apparatus further including an actuating member slidably disposed with respect to said support assembly and adapted for reciprocating movement along an axis parallel to respective longitudinal axes of said first and second pumps, said actuating member engaging said second pump plunger member and said first pump barrel portion, whereby movement of said actuating member in a first operating direction causes said actuating member to simultaneously engage said first pump in a suction stroke and said second pump in a pumping stroke and, and whereby movement of said actuating member in a second operating direction, opposite to said first direction, causes said actuating member to simultaneously engage said first pump in a pumping stroke and said second pump in a suction stroke.

2. The pumping apparatus of claim 1, wherein said first and second pumps are syringe pumps.

3. The pumping apparatus of claim 1, wherein said apparatus includes a yoke operatively driven by said actuating member, the yoke having a carriage portion which engages the barrel portion of one of said two pumps, said yoke further having an arm portion which engages the plunger member of the other of said two pumps.

4. The pumping apparatus of claim 1, wherein said housing includes first and second channels, the first channel receiving said first pump and the second channel receiving said second pump, each of said first and second channels being divided into two separate chamber portions by a dividing wall located within said channels between end portions of said channels, said first channel dividing wall having an opening therein which receives said first pump barrel portion and said second channel dividing wall having an opening which receives said second pump plunger member, whereby said first pump barrel portion may move between said two chamber portions of said first channel, and said second pump plunger member may move between said two chamber portions of said second channel in accordance with movement of said actuating member.

5. The pumping apparatus of claim 4, wherein said second channel dividing wall restrains said second pump barrel portion from any significant movement.

6. The pumping apparatus of claim 1, further including a fluid powered cylinder operatively connected to said actuating member.

7. The pumping apparatus of claim 6, wherein said fluid powered cylinder is a pneumatic cylinder.

8. The pumping apparatus of claim 6, wherein said actuating member fluid cylinder has a single-stroke, double-ended piston slidable therein.

9. The pumping apparatus of claim 1, wherein said housing includes first and second channels which respectively receive said first and second pumps, said first channel engaging said first pump plunger member to restrain said first pump plunger member from movement when said first pump barrel portion moves within said first channel in response to movement of said actuating member, said second channel engaging said second pump barrel portion to restrain said second pump barrel portion from movement within said second channel whereby said second pump plunger member moves within said second channel in response to movement of said actuating member.

10. The pumping apparatus of claim 9, wherein said actuating member includes a yoke, said yoke having first and second portions extending therefrom, said yoke first portion engaging said second pump plunger member and said yoke second portion engaging said first pump barrel portion.

11. The pumping apparatus of claim 9, wherein each of said first and second channels are divided into two separate chamber portions by a dividing wall located within said channels between end portions of said channels, said first channel dividing wall having an opening therein which receives said first pump barrel portion, whereby said first pump barrel portion may move between said two chamber portions of said first channel, said second channel dividing wall having an opening which receives said second pump plunger member, whereby said second pump plunger member may move between said two chamber portions of said second channel in accordance with movement of said actuating member.

12. The pumping apparatus of claim 11, wherein said second channel dividing wall restrains said second pump barrel portion from any significant movement.

13. The pumping apparatus of claim 11, wherein said support assembly first channel includes an end wall, the first channel end wall engaging said first pump plunger member to restrain said first pump plunger member from movement.

14. A pumping apparatus for pumping blood comprising:
a housing,
first and second pumps disposed within the housing, each of the two pumps having an elongated barrel defining a pump chamber therein and further having a plunger slidable received within said pump chamber;
an actuating assembly for simultaneously actuating each of said first and second pumps, the actuating assembly operatively engaging said first and second pumps, the actuating assembly including a fluid cylinder for driving said actuating assembly between two operative positions, said actuating assembly engaging said first pump barrel portion and said second pump plunger member, whereby movement of said actuating assembly in a first direction in response to said fluid cylinder effects a pumping stroke in said first pump and an intake stroke in said second pump, and whereby movement of said actuating assembly in a second direction in response to said fluid cylinder effects an intake stroke in said first pump and a pumping stroke in said second pump; and,
said housing includes two parallel channels extending longitudinally therein between two end portions of said housing, said two channels including means for restraining a part of each of said two pumps.

15. The pumping apparatus of claim 14, wherein each of said two channels includes a dividing wall, the dividing walls respectively defining two chambers in each of said two channels, one of said plunger and barrel of each of said two pumps being received within respective first and second chambers of each channel.

16. The pumping apparatus of claim 14, wherein said fluid cylinder is a single-ended, double-acting pneumatic cylinder.

17. The pumping apparatus of claim 14, wherein said first channel dividing wall includes an opening which receives said first pump barrel portion which permits slidable movement of said first pump barrel portion between said first channel two chambers.

18. The pumping apparatus of claim 14, wherein each of said channels includes distinct first and second chamber portions thereof, said first chamber portions of said two channels communicating with each other.

19. The pumping apparatus of claim 14, wherein said actuating assembly includes a link interconnecting an actuating rod with said first pump barrel and said second pump plunger.

20. The pumping apparatus of claim 14, wherein each of said syringe pumps are syringe pumps.

21. The pumping apparatus of claim 20, wherein said syringe pumps are disposed on said housing parallel to each other.

22. The pumping apparatus of claim 20, wherein said actuating assembly includes a yoke, said yoke having first and second portions extending therefrom, said yoke first portion engaging said second pump plunger member and said yoke second portion engaging said first pump barrel portion.

23. A pumping apparatus for pumping blood comprising:
first and second syringe pumps, each of the two syringe pumps having a barrel portion defining a pump chamber therein and said pumps further having a plunger member slidably received within said pump chamber;
a base member supporting said first and second pumps, said base fixedly engaging said first syringe pump plunger member and said second syringe pump barrel portion, whereby said first and second syringe pumps are actuated by movement of said first syringe pump barrel portion relative to said first syringe pump plunger member and second syringe pump plunger member relative to said second syringe pump barrel portion;
an actuating assembly for simultaneously actuating each of said first and second pumps in alternating pumping and suction strokes, the actuating assembly operatively engaging said first syringe pump barrel portion and said second syringe pump plunger member, said actuating assembly including a fluid-powered cylinder for driving said actuating assembly in a reciprocating path between two operative positions, whereby movement of said actuating assembly in a first direction causes said actuating assembly to drive said first syringe pump in a suction stroke and to simultaneously engage said second syringe pump in a pumping stroke, and whereby movement of said actuating assembly in a second direction causes said actuating assembly to drive said first pump in a pumping stroke and to engage said second syringe pump in a suction stroke.

* * * * *